(12) United States Patent
Papaioannou et al.

(10) Patent No.: US 12,033,740 B2
(45) Date of Patent: Jul. 9, 2024

(54) SYSTEMS AND METHODS FOR ROBUST AND AUTOMATIC FACE DE-IDENTIFICATION FOR CT AND MRI

(71) Applicants: Vasileios K. Papaioannou, Baltimore, MD (US); Quan Chen, Lexington, KY (US); Xue Feng, Lexington, KY (US)

(72) Inventors: Vasileios K. Papaioannou, Baltimore, MD (US); Quan Chen, Lexington, KY (US); Xue Feng, Lexington, KY (US)

( * ) Notice: Subject to any disclaimer, the term of this patent is extended or adjusted under 35 U.S.C. 154(b) by 466 days.

(21) Appl. No.: 17/542,409

(22) Filed: Dec. 4, 2021

(65) Prior Publication Data

US 2023/0178218 A1 Jun. 8, 2023

(51) Int. Cl.
*G16H 30/20* (2018.01)
*G16H 30/40* (2018.01)

(52) U.S. Cl.
CPC ............. *G16H 30/20* (2018.01); *G16H 30/40* (2018.01)

(58) Field of Classification Search
CPC .............................. G16H 30/20; G16H 30/40
See application file for complete search history.

(56) References Cited

U.S. PATENT DOCUMENTS

| | | | |
|---|---|---|---|
| 9,269,140 B2 * | 2/2016 | Machado | A61B 5/0042 |
| 2007/0081700 A1 * | 4/2007 | Blumenfeld | G16H 30/20 |
| | | | 382/128 |
| 2009/0285357 A1 * | 11/2009 | Khamene | A61B 6/5217 |
| | | | 378/207 |
| 2011/0161112 A1 * | 6/2011 | Keefe | G16H 40/67 |
| | | | 705/3 |
| 2012/0035463 A1 * | 2/2012 | Pekar | G06T 7/149 |
| | | | 600/411 |
| 2013/0223687 A1 * | 8/2013 | Kimoto | G06T 7/155 |
| | | | 382/103 |
| 2014/0046601 A1 * | 2/2014 | Carlsson | A61N 5/1075 |
| | | | 702/19 |
| 2015/0262014 A1 * | 9/2015 | Iwamura | G16H 50/20 |
| | | | 382/128 |
| 2016/0155236 A1 * | 6/2016 | Davey | G06T 15/08 |
| | | | 382/131 |
| 2016/0324664 A1 * | 11/2016 | Piron | A61F 2/4601 |
| 2016/0354155 A1 * | 12/2016 | Hodges | A61B 34/20 |
| 2017/0135655 A1 * | 5/2017 | Wang | A61B 5/0035 |
| 2017/0255751 A1 * | 9/2017 | Sanmugalingham | |
| | | | G06F 21/6254 |
| 2019/0172570 A1 * | 6/2019 | Popescu | G16H 30/20 |
| 2019/0192099 A1 * | 6/2019 | Jia | G06T 7/155 |
| 2020/0027264 A1 * | 1/2020 | Chen | G06T 7/344 |
| 2020/0273148 A1 * | 8/2020 | Ouyang | G06T 7/564 |
| 2020/0320775 A1 * | 10/2020 | Holladay | G06T 7/11 |
| 2022/0031565 A1 * | 2/2022 | Yim | A61H 39/002 |
| 2022/0146498 A1 * | 5/2022 | Vanapalli | B01L 3/50273 |
| 2022/0198750 A1 * | 6/2022 | Zhou | G06T 3/16 |

* cited by examiner

Primary Examiner — Dominic E Rego

(57) ABSTRACT

The present disclosure relates to a method and apparatus for robust and automatic face de-identification from CT and MRI. The method includes: receiving DICOM files of patient bodies obtained by a CT or MRI system; normalizing the images; extracting the heads from bodies; creating face masks; and writing DICOM files back with de-identified faces.

11 Claims, 4 Drawing Sheets

Normalization & Head Extraction
Face Mask Creation
Write Back to DICOM
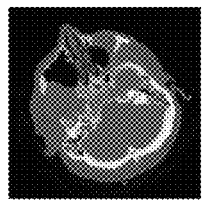
FIG. 3A
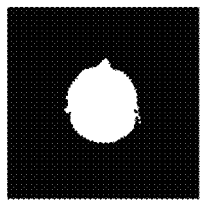
FIG. 3D
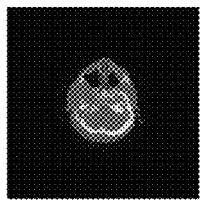
FIG. 3L
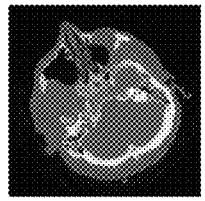
FIG. 3M
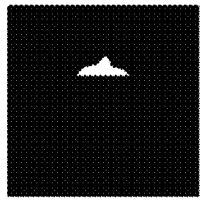
FIG. 3B
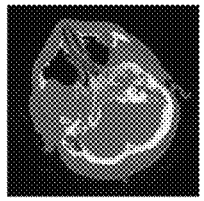
FIG. 3E
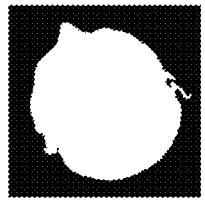
FIG. 3K
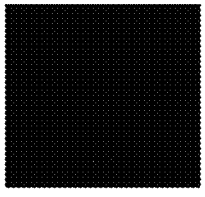
FIG. 3N
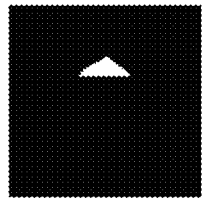
FIG. 3C
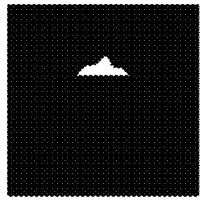
FIG. 3F
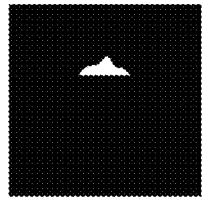
FIG. 3J
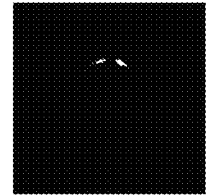
FIG. 3G
FIG. 3I
FIG. 3H
FIG. 3

SYSTEMS AND METHODS FOR ROBUST AND AUTOMATIC FACE DE-IDENTIFICATION FOR CT AND MRI

STATEMENT OF GOVERNMENT INTEREST

This invention was made with government support under Grant No. R44CA254844 awarded by The National Institute of Health. The government has certain rights in the invention.

CROSS-REFERENCE TO RELATED APPLICATION

Not applicable.

FIELD

This disclosure relates to computed tomography (CT) and Magnetic Resonance Imaging (MRI) operations that develop and validate a robust and automatic face de-identification from CT and MRI.

BACKGROUND

A key step in clinical and research practice is to de-identify patient face data in medical images to protect their personal information. However, there is value in utilizing these data beyond specific patients/treatments to aid in the improvement of current practices and patient outcomes. It is therefore vital to anonymize such data with minimal distortion. For face anonymization, existing approaches involve Gaussian filters, face distortion via deep learning, or simple human intervention aided by software that blurs or adds/removes patches. Each approach poses unique challenges. Gaussian filters intervene directly on the face and corrupt images with no guarantee of full de-identification. Deep learning strategies are complex and time-consuming, require expert-level fine-tuning, and specialized hardware. Manual intervention approaches are slow and susceptible to bias and human error. The present disclosure was designed to overcome all of the issues faced by existing approaches.

SUMMARY

Examples of the present disclosure provide a method for robust and automatic face de-identification from CT and MRI.

According to the first aspect of the present disclosure, a computer-implemented method for robust and automatic face de-identification from CT and MRI. The method may include receiving DICOM files of patient bodies obtained by a CT or MRI system, normalizing the images, extracting the heads from the bodies, creating face masks, and writing DICOM files back with de-identified faces.

According to the second aspect of the present disclosure, an apparatus for robust and automatic face de-identification from CT and MRI. The apparatus may include one or more processors, a display, and a non-transitory computer-readable memory storing instructions executable by one or more processors. Wherein the instructions are configured to receive DICOM files of patient bodies obtained by a CT or MRI system, normalize the images, extract the heads from the bodies, create face masks, and write DICOM files back with de-identified faces.

According to a third aspect of an example of the present disclosure, a non-transitory computer-readable storage medium having stored therein instructions is provided. When the instructions are executed by one or more processors or one or more graphic processing units (GPUs) of the apparatus, the instructions cause the apparatus to receive DICOM files of patient bodies obtained by a CT or MRI system, normalize the images, extract the heads from the bodies, create face masks, and write DICOM files back with de-identified faces.

Other aspects and features according to the example embodiment of the disclosed technology will become apparent to those of ordinary skill in the art, upon reviewing the following detailed description in conjunction with the accompanying figures.

BRIEF DESCRIPTION OF THE DRAWINGS

The patent or application file contains at least one drawing executed in color. Copies of this patent or patent application publication with color drawings(s) will be provided by the Office upon request and payment of the necessary fee.

Reference will now be made to the accompanying drawings, which are not necessarily drawn to scale.

FIG. 3 illustrates the whole workflow, according to an example of the present disclosure.

FIG. 3A displays one axial slice of the 3D CT images serving as an example to explain pictorially the present disclosure.

FIG. 3B shows image in FIG. 3A transformed to patient coordinate system.

FIG. 3C shows the segmentation of the CT image in FIG. 3B.

FIG. 3D presents the result of centering and aligning the segmentation and the original image along the posterior-anterior direction.

FIG. 3E demonstrates removing parts of the head that are irrelevant to face anonymization.

FIG. 3F displays the black top-hat of FIG. 3E.

FIG. 3G exhibits the outcome of filling in the holes detected by the black top-hat operator.

FIG. 3H portrays the detected cavities, if any.

FIG. 3I is the result of filling these cavities.

FIG. 3J displays the convex hull of FIG. 3I.

FIG. 3K shows the desired face mask as a subtraction of FIG. 3I from FIG. 3J.

FIG. 3L presents the border between the face mask and the face.

FIG. 3M demonstrates the face mask and border embedded properly into the image.

FIG. 3N is the masked image back to its original coordinate system, center and orientation.

FIG. 4A is a scatter plot of the segmentation area versus slice index. The area increases from bottom to top and the segmented slices index increases from left to right or, equivalently, from feet to head.

FIG. 4B shows the slice with the maximum area detected in FIG. 4A.

FIG. 4C shows the slices with the minimum on area either side of the maximum-area slice in FIG. 4B.

FIG. 4D depicts the areas corresponding to the head. The leftmost vertical line denotes the bottom of the head and the rightmost the top of the head.

DETAILED DESCRIPTION

Reference will now be made in detail to example embodiment, examples of which are illustrated in the accompanying drawings. The following description refers to the accompanying drawings in which the same numbers in different drawings represent the same or similar elements unless otherwise represented. The implementations set forth in the following description of exemplary embodiments do not represent all implementations consistent with the disclosure. Instead, they are merely examples of apparatuses and methods consistent with aspects related to the disclosure as recited in the appended claims.

The terminology used in the present disclosure is for the purpose of describing particular embodiments only and is not intended to limit the present disclosure. As used in the present disclosure and the appended claims, the singular forms "a," "an," and "the" are intended to include the plural forms as well, unless the context clearly indicates otherwise. It shall also be understood that the term "and/or" used herein is intended to signify and include any or all possible combinations of one or more of the associated listed items.

It shall be understood that, although the terms "first," "second," "third," etc. may be used herein to describe various information, the information should not be limited by these terms. These terms are only used to distinguish one category of information from another. For example, without departing from the scope of the present disclosure, first information may be termed as second information; and similarly, second information may also be termed as first information. As used herein, the term "if" may be understood to mean "when" or "upon" or "in response to a judgment" depending on the context.

The present disclosure related to an algorithm for robust and automatic face de-identification from CT and MRI. The disclosure is not limited to the face and can be easily extended to other body parts and objects.

Figure 1:
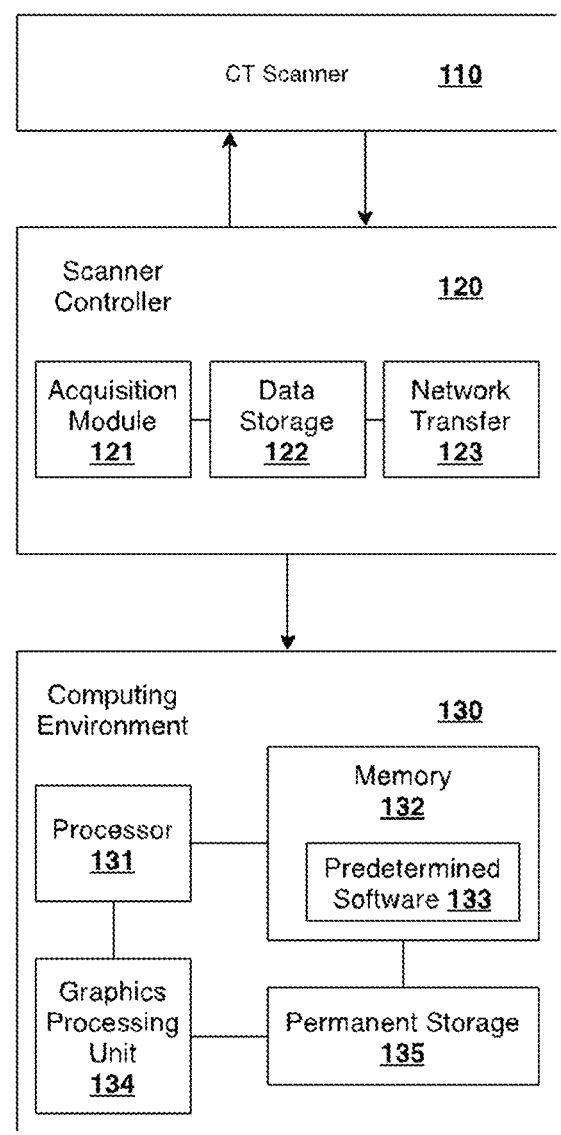
FIG. 1 is a system diagram of CT scanner, controller, and computing environment illustrating an operating environment capable of implementing aspects of the present disclosure.

FIG. 1 shows a system diagram of CT scanner 110, controller 120 and computing environment 130. The CT scanner 110 is used to obtain CT images covering the head region of a subject and is controlled by the scanner controller 120. The scanner controller 120 contains the acquisition module 121 that drives the CT scanner 110, the data storage module 122 that stores the CT images of different subjects, and the network transfer module 123 that sends the CT images to another computing environment 130. The computing environment 130 contains processor 131, GPU 134, memory 132, and permanent storage 135 to perform given directions. In executing the directions, the predetermined software 133 is loaded into memory 132 and executed by processor 131 to yield the desired output.

The processing component 120 typically controls overall operations of the computing environment 130, such as the operations associated with display, data acquisition, data communications, and image processing. The processor 131 may include one or more processors to execute instructions to perform all or some of the steps in the above-described methods. Moreover, the processor 131 may include one or more modules which facilitate the interaction between the processor 131 and other components. The processor may be a Central Processing Unit (CPU), a microprocessor, a single chip machine, a GPU, or the like. GPU 134 can include one or more GPUs interconnected to execute one or more GPU executable programs.

The memory 132 is configured to store various types of data to support the operation of the computing environment 130. Examples of such data comprise instructions for any applications or methods operated on the computing environment 130, CT datasets, image data, etc. The memory 132 may be implemented by using any type of volatile or non-volatile memory devices, or a combination thereof, such as a static random-access memory (SRAM), an electrically erasable programmable read-only memory (EEPROM), an erasable programmable read-only memory (EPROM), a programmable read-only memory (PROM), a read-only memory (ROM), a magnetic memory, a flash memory, a magnetic or optical disk.

In an embodiment, the computing environment 130 may be implemented with one or more application specific integrated circuits (ASICs), digital signal processors (DSPs), digital signal processing devices (DSPDs), programmable logic devices (PLDs), field programmable gate arrays (FPGAs), graphical processing units (GPUs), controllers, micro-controllers, microprocessors, or other electronic components, for performing the above methods.

The method for robust and automatic face de-identification from CT and MRI is programmed as one set of predetermined software 133 and installed on the computing environment 130. When the computing environment 130 receives CT images from scanner controller 120, the predetermined software 133 is executed to generate the face anonymization results.

Figure 2:
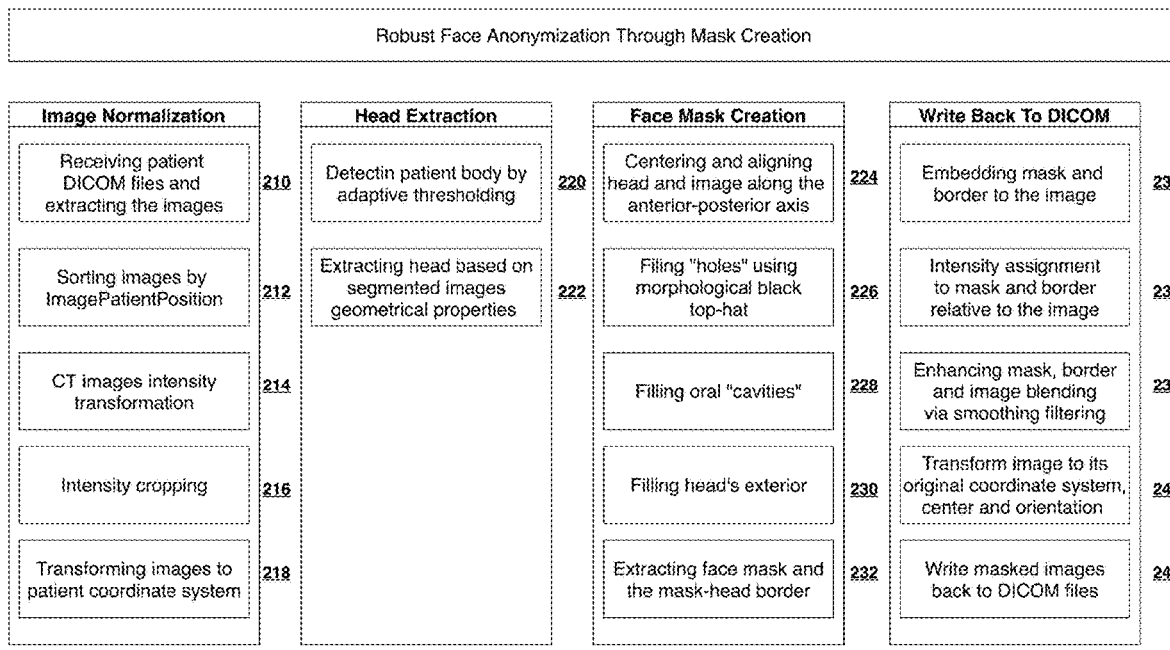
FIG. 2 is a flow chart illustrating a method for robust and automatic face de-identification from CT and MRI according to an example of the present disclosure.

FIG. 2 shows an example flow chart setting forth the steps of a method 200 in accordance with the present disclosure.

In step 210, DICOM files of the patient body covering the head are received and the related 3D CT or MRI images are extracted. For example, one axial slice of the 3D CT images is shown in FIG. 3A.

In step 212, these images are sorted by the DICOM "Image Position (Patient)" attribute along the superior-inferior axis.

In step 214, a rescale intercept and slopet, obtained from the DICOM file, are applied to convert from stored units to output units for CT images.

In step 216, image intensities are cropped i.e. image intensity is restricted to a minimum and maximum value based on image modality.

In step 218, the images are transformed to the patient coordinate system so that the nose is aligned towards the anterior direction, FIG. 3B.

Figure 4:
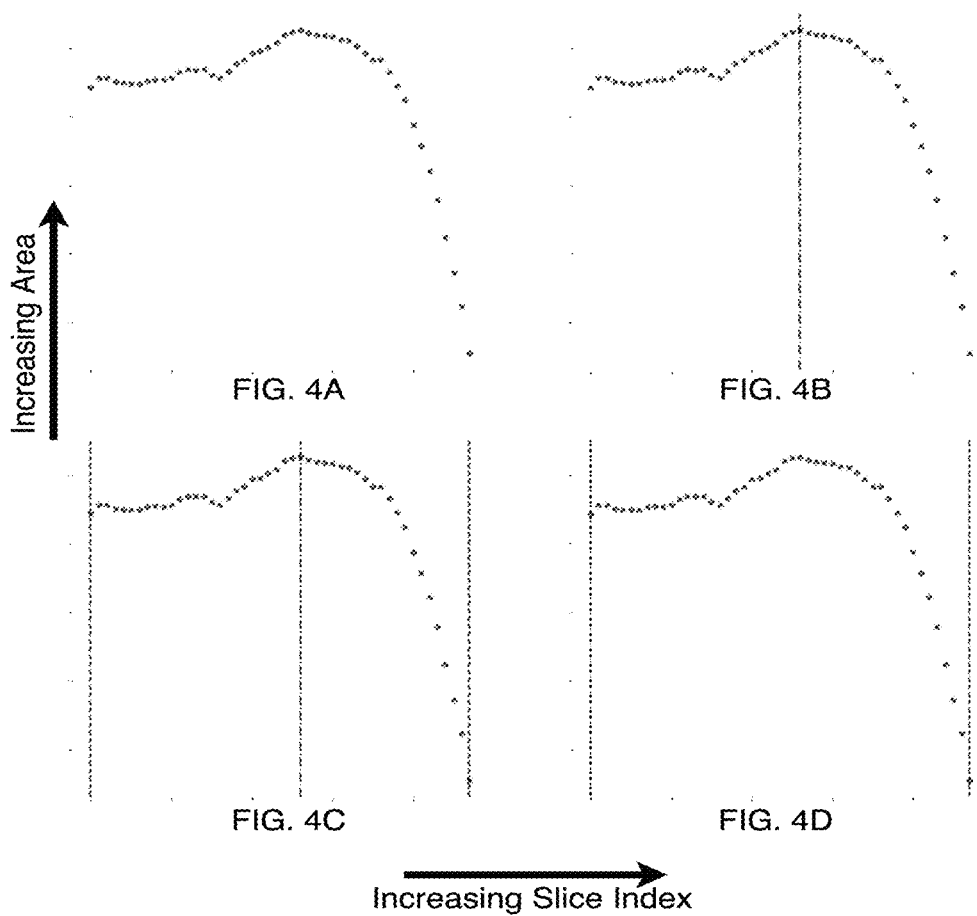
FIG. 4 illustrates head detection based on segmented image area, according to an example of the present disclosure.

In step 220, the body is detected using adaptive thresholding, as shown in FIG. 3C In step 222, the head is extracted from the body based on segmented images' geometric properties. Specifically, it is expected from human head anatomy that the slice area will increase from the neck to the nose and decrease from the nose to the top of the head, as seen in FIG. 4A. Therefore, the slice located above the "nose" slice that has the smallest non-zero area corresponds to the top of the head. Similarly, the slice located below the "nose" slice that has the smallest non-zero area denotes the bottom of the head. In addition, it is anticipated, especially for MRI images, that only part of the head is captured by the image. In these cases, it might happen that the "nose" slice coincides with either the bottom or the top of the head. Further, it is possible that the nose is not part of the head captured by the image. The algorithm can handle these cases since the key is to detect the slice with the largest area no matter which part of the head is captured. FIG. 4B shows which slice has the maximum area, while FIG. 4C and FIG. 4D display which slices have the minimum area either side of the "nose" slice. Finally, it is also possible that the body region apart from the head is present in the images. This is solved by taking in account the anatomic fact that the area for slices below the neck increases up to the shoulder level and then it decreases. Hence, through maximum/minimum slice area selection, and how the slice area changes between these points, the algorithm can precisely distinguish the head from the body.

In step 224, the segmented slice and corresponding image are centered and aligned along the anterior-posterior axis, if needed. To examine whether centering is needed, the distance between the image center and the segmentation centroid is compared against the distances between the image corners and the segmentation centroid. If the image center-segmentation centroid distance is the least among the five measured distances, then no centering is needed. Otherwise, the image is extended by zero-padding along the corner that is closest to the centroid so that the centroid coincides with the center of the newly extended image.

To determine if an image needs to be rotated to achieve the anterior-posterior axis alignment of the nose, the angle between the major axis of an equivalent ellipsoid and the anterior-posterior axis is calculated. It is likely that the calculated angle will not be the same for all slices and that some angles will rotate the segmented object beyond the desired axis. To alleviate these potential issues, all slices are rotated by the median of the calculated angles. If the median angle is less than 10 degrees, no rotation takes place. Prior to rotation, the image is doubled in size with zero-padding so that the final rotated segmentation will be within the image. This step is not required if centering was performed earlier. The final result is presented in FIG. 3D. Here, the figure appears to be "zoomed out" due to the doubled image size.

In step 226, any holes are filled in using a morphological black top-hat. As holes are meant background areas of relatively small size that are enclosed by foreground areas. First, the slices located right in front of the face and right at the back of the head are detected by finding the first slices with at least one non-background pixel when parsing the image from the anterior-posterior and posterior-anterior directions, respectively. This allows the algorithm to omit processing parts of the head that are far away from the face, as well as background slices, and thus speed up the algorithm and reduce the resources needed. Here, a slice is considered "far away", if its distance from the front of the face is larger than 25% of the distance between the front and the back of the head, as illustrated in FIG. 3E. Following the selection of slices to process, a black top-hat is calculated, as shown in FIG. 3F. The black top-hat provides the locations of holes up to a certain size and is defined as $$T_b(I) = I \cdot D_8 - I,$$

where I denotes the image, $D_8$ denotes a disk of radius 8 in pixels, and $I \cdot D_8$ is the closing operation of the image and disk. In this transformation, all holes up to radius 8 pixels are detected. The value of the radius size can be updated per the image needs. Finding and filling holes in the original image segmentation ensures that the face mask will leave the head intact. In FIG. 3F, the black top-hat is totally black because there are no holes. Therefore, the final result shown in FIG. 3G is the same as FIG. 3E before applying the black top-hat.

In step 228 the cavities of the segmented head are filled in. As cavities are meant background areas of arbitrary size that might be or not connected to the background region outside of the head. These cavities for example might correspond to oral cavities when the mouth is open during scanning. Their detection can happen by adding together the inverse of the segmentation and the inverse of the convex hull of the segmentation. Any cavities will have a value of 1 where the background will have a value of 0 and the foreground will have a value of 2. The detected cavities are shown in FIG. 3H and the corresponding result in FIG. 3I. FIG. 3I is exactly the same as FIG. 3G because the detected cavities are outside of the head.

In step 230, the exterior of the head is filled in by means of the convex hull of the head for the x-y plane and is shown in FIG. 3J.

In step 232, subtracting the head from the convex hull results in the desired face mask. Next, the mask is expanded with the aid of a morphological dilation along the anterior-posterior axis using a rectangular structural element of size 10×1 pixels, $R_{10,1}$.

At this point, the mask anonymizes the face, but could still retain some identifying facial characteristics. These retaining features will become apparent after 3D reconstruction. To counter that, a second convex hull of the mask is found on the y-z plane and the anonymized face is subtracted from that to remove any further identifying facial features. The final result is shown in FIG. 3K.

Moreover, the border between the mask and head is found using their morphological gradient and is illustrated in FIG. 3L. Finding the border enables further control over making the mask indistinguishable from the head.

In step 234, the acquired mask and border are embedded into the image.

In step 236, the embedded elements are assigned an intensity relative to the slice on which they are applied.

In step 238, the face mask and the head are blended better using a two-dimensional Gaussian filter using a sigma value of 3. The sigma value changed as needed. The overall result is shown in FIG. 3M.

Finally, in step 240, the masked image is transformed back to the original coordinate system, center and orientation. The final result is displayed in FIG. 3N.

Figure 5:
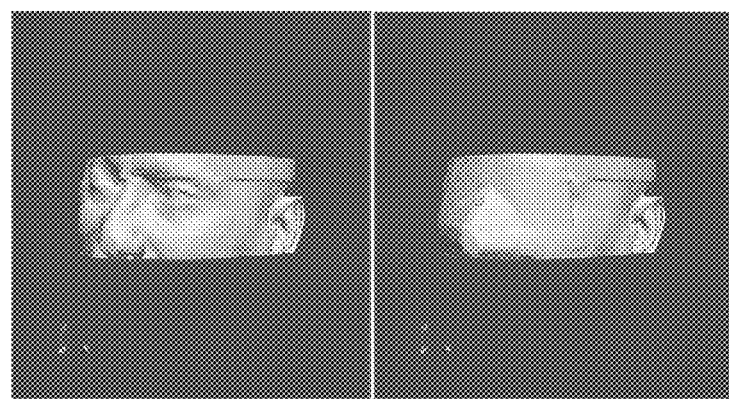
FIG. 5 demonstrates the 3D reconstruction of the original 3D CT image and the face mask.

FIG. 5 shows a 3D reconstruction of the original 3D CT image on the left, and on the right shows the 3D reconstruction of the face mask applied over the face. Here, the face is fully covered while remaining intact.

What is claimed is:

1. A computer-implemented method for robust and automatic face de-identification from CT and MRI using one or more processors, the method comprising:
receiving DICOM files of patient bodies obtained by a CT or MRI system; extracting the related 3D images and sorting them along the superior-inferior axis based on the "Image Position (Patient)" attribute; converting CT images from stored units to output units through rescale intercept and rescale slope; applying intensity cropping; transforming the images to patient coordinate system; detecting the body using adaptive thresholding and consequently extracting the head from it on the basis of geometric properties; centering and aligning the head and image along the anterior-posterior axis if needed; filling any holes and cavities found in the segmented head; calculating the convex hull for the x-y plane; extracting the face anonymizing mask by subtracting the head from its convex hull; expanding the mask along the anterior-posterior direction; enhancing the face mask with its convex hull on y-z plane; calculating the border separating the mask from the face; embedding both the mask and the border into the original images; setting the intensity values of the mask and the border so to be indistinguishable from the corresponding head slice; applying a smoothing filter to enhance blending; transforming back the masked image to its original orientation, center and coordinate system; writing the processed images back to the original DICOM files.

2. The computer-implemented method for robust and automatic face de-identification from CT and MRI according to claim 1, normalizing the images further comprises:
extracting images from DICOM files; sorting images by the x, y, and z coordinates of the upper left-hand corners of the images; converting stored values to output units for CT images; applying intensity cropping; and transforming images to the patient coordinate system such that patient noses are aligned towards the posterior-anterior direction.

3. The computer-implemented method for robust and automatic face de-identification from CT and MRI according to claim 1, extracting the heads from bodies further comprises:
detecting patients' bodies through adaptive thresholding; and extracting heads from body segmentations based on geometrical properties of the segmented images.

4. The computer-implemented method for robust and automatic face de-identification from CT and MRI according to claim 1, creating face masks further comprises:
centering and aligning heads along the anterior-posterior axis using an affine transformation; filling in head holes and cavities using a morphological black top-hat as well as inverted versions of the segmentation and its convex hull respectively; creating face masks from heads' convex hulls; extracting the boundaries between masks and heads; embedding face masks and borders into the original head images; assigning embedded mask regions an intensity value relevant to the corresponding head images; enhancing masks and head blending by applying a smoothing filter over the border regions.

5. The computer-implemented method for robust and automatic face de-identification from CT and MRI according to claim 1, transforming back the masked image to its original orientation, center and coordinate system; writing DICOM files back with de-identified faces.

6. An apparatus for robust and automatic face de-identification from CT and MRI, comprising:
one or more processors;
a display; and
a non-transitory computer readable memory storing instructions executable by the one or more processors, wherein the instructions are configured to:
receive DICOM files of patient bodies obtained by a CT or MRI system; extract the related 3D images and sort them along the superior-inferior axis based on the "Image Position (Patient)" attribute; convert CT images from stored units to output units through rescale intercept and rescale slope; apply intensity cropping; transforming the images to patient coordinate system; detect the body using adaptive thresholding and consequently extracting the head from it on the basis of geometric properties; center and align the head and image along the anterior-posterior axis if needed; fill any holes and cavities found in the segmented head; calculate the convex hull for the x-y plane; extract the face anonymizing mask by subtracting the head from its convex hull; expand the mask along the anterior-posterior direction; enhance the face mask with its convex hull on y-z plane; calculate the border separating the mask from the face; embed both the mask and the border into the original images; set the intensity values of the mask and the border so to be indistinguishable from the corresponding head slice; apply a smoothing filter to enhance blending; transform back the masked image to its original orientation, center and coordinate system; write the processed images back to the original DICOM files.

7. The apparatus for robust and automatic face de-identification from CT and MRI according to claim 6, normalizing the images further comprises:
extracting images from DICOM files; sorting images by the x, y, and z coordinates of the upper left-hand corners of the images; converting stored values to output units for CT images; applying intensity cropping; and transforming images to the patient coordinate system such that patient noses are aligned towards the posterior-anterior direction.

8. The apparatus for robust and automatic face de-identification from CT and MRI according to claim 6, extracting the heads from bodies further comprises:
detecting patients' bodies through adaptive thresholding; and extracting heads from body segmentations based on geometrical properties of the segmented images.

9. The apparatus for robust and automatic face de-identification from CT and MRI according to claim 6, creating face masks further comprises:
centering and aligning heads and images along the anterior-posterior axis using an affine transformation; filling in head holes and cavities using a morphological black top-hat as well as inverted versions of the segmentations and segmentation convex hulls respectively; creating face masks from heads' convex hulls; extracting the boundaries between masks and heads; embedding face masks and borders into the original head images; assigning embedded mask regions an intensity value relevant to the corresponding head images; and enhancing masks and head blending by applying a smoothing filter over the border regions.

10. The apparatus for robust and automatic face de-identification from CT and MRI according to claim 6, writing DICOM files back with de-identified faces:
aligning back the masked images along their original orientations, center and coordinate system; and writing images back to DICOM files.

11. A non-transitory computer-readable storage medium having stored therein instructions that, when executed by one or more processors of an apparatus causing the apparatus to perform acts comprising:
receiving DICOM files of patient bodies obtained by a CT or MRI system; extracting the related 3D images and sorting them along the superior-inferior axis based on the "Image Position (Patient)" attribute; converting CT images from stored units to output units through rescale intercept and rescale slope; applying intensity cropping; transforming the images to patient coordinate system; detecting the body using adaptive thresholding and consequently extracting the head from it on the basis of geometric properties; centering and aligning the head and image along the anterior-posterior axis if needed; filling any holes and cavities found in the segmented head; calculating the convex hull for the x-y plane; extracting the face anonymizing mask by subtracting the head from its convex hull; expanding the mask along the anterior-posterior direction; enhancing the face mask with its convex hull on y-z plane; calculating the border separating the mask from the face; embedding both the mask and the border into the original images; setting the intensity values of the mask and the border so to be indistinguishable from the corresponding head slice; applying a smoothing filter to enhance blending; transforming back the masked image to its original orientation, center and coordinate system; writing the processed images back to the original DICOM files.

\* \* \* \* \*